United States Patent [19]

Camaggi et al.

[11] Patent Number: 5,051,440
[45] Date of Patent: Sep. 24, 1991

[54] NITROGEN-CONTAINING HETEROCYCLIC COMPOUNDS WITH ANTIFUNGAL ACTION, USE AND A COMPOSITION THEREOF

[75] Inventors: Giovanni Camaggi, Novara; Lucio Filippini, Saronno; Carlo Garavaglia, Cuggiono; Luigi Mirenna; Isabella Venturini, both of Milan, all of Italy

[73] Assignee: Presidenza Del Consiglio Dei Ministri, Rome, Italy

[21] Appl. No.: 370,910

[22] Filed: Jun. 21, 1990

[30] Foreign Application Priority Data

Jun. 23, 1988 [IT] Italy ............................ 21077 A/88

[51] Int. Cl.$^5$ .................... A01N 43/50; C07D 233/60
[52] U.S. Cl. .................... 514/399; 514/256; 514/400; 514/383; 514/341; 514/354; 548/341; 548/343; 548/266.8; 546/278; 546/316; 544/333
[58] Field of Search ............... 548/341; 514/399, 341; 546/278

[56] References Cited

U.S. PATENT DOCUMENTS

| | | | |
|---|---|---|---|
| 4,609,669 | 9/1986 | Kume et al. | 548/341 |
| 4,678,798 | 7/1987 | Rentzea et al. | 548/341 |
| 4,708,960 | 11/1987 | Rentzea et al. | 548/341 |

Primary Examiner—Jane T. Fan
Attorney, Agent, or Firm—Morgan & Finnegan

[57] ABSTRACT

Nitrogen-containing heterocyclic compounds endowed with antifungal action, which have the general formula:

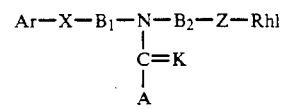

wherein:
Ar = phenyl, optionally substituted with halogens, $(C_1-C_3)$-alkyls, $(C_1-C_3)$-haloalkyls, $(C_2-C_4)$-alkenyls, $(C_2-C_4)$-haloalkenyls, $(C_1-C_3)$-alkoxy groups, $(C_1-C_4)$-haloalkoxy groups; pyridyl, optionally substituted with one or more halogens or with $(C_1-C_3)$-haloalkyls;
K, X, Z = O or S;
$B_1$, $B_2$ = $(C_1-C_6)$-alkylidenes;
Rhl = $(C_1-C_6)$-haloalkyl, $(C_2-C_8)$-haloalkenyl, $(C_3-C_8)$-haloalkoxyalkyls, $(C_3-C_8)$-haloalkoxyalkenyls;
A represents a group selected from among

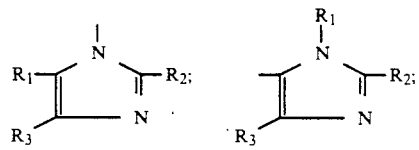

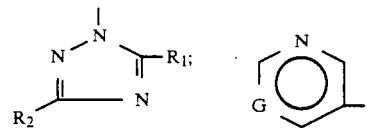

wherein;
$R_1$, $R_2$, $R_3$ = H, $(C_1-C_6)$-alkyls, $(C_1-C_6)$-haloalkyls, $(C_2-C_6)$-alkenyls, $(C_2-C_6)$-haloalkenyls, $(C_2-C_6)$-alkinyls, $(C_2-C_6)$-haloalkinyls; and
G = CH or N.

12 Claims, No Drawings

NITROGEN-CONTAINING HETEROCYCLIC COMPOUNDS WITH ANTIFUNGAL ACTION, USE AND A COMPOSITION THEREOF

DESCRIPTION OF THE INVENTION

The present invention relates to nitrogen-containing heterocyclic compounds endowed with a high antifungal activity, to the process for preparing them and to their use in the agrarian field as fungicides.

Therefore, an object of the present invention is the provision of compounds having the general formula:

$$\text{Ar}-\text{X}-\text{B}_1-\underset{\underset{A}{\overset{\|}{\text{C}=\text{K}}}}{\text{N}}-\text{B}_2-\text{Z}-\text{Rhl} \quad (I)$$

wherein:
- Ar represents a phenyl; a phenyl substituted with one or more halogens, $(C_1-C_3)$-alkyls, $(C_1-C_3)$-haloalkyls, $(C_2-C_4)$-alkenyls, $(C_2-C_4)$-haloalkenyls, $(C_1-C_3)$-alkoxy groups, $(C_1-C_4)$-haloalkoxy groups; a pyridyl, a pyridyl optionally substituted with one or more halogens or with $(C_1-C_3)$-haloalkyls;
- K, X, Z are, independently of each other, either O or S;
- $B_1$, $B_2$ which may be equal to, or different from, each other, are linear or branched $(C_1-C_6)$-alkylidenes;
- Rhl represents a $(C_1-C_6)$-haloalkyl containing from 1 to 9 halogen atoms, a $(C_2-C_8)$-haloalkenyl containing from 1 to 9 halogen atoms, $(C_3-C_8)$-haloalkoxyalkyls, $(C_3-C_8)$-haloalkoxyalkenyls, with the halogen being preferably fluorine;
- A represents a nitrogen-containing heterocyclic group selected from among:

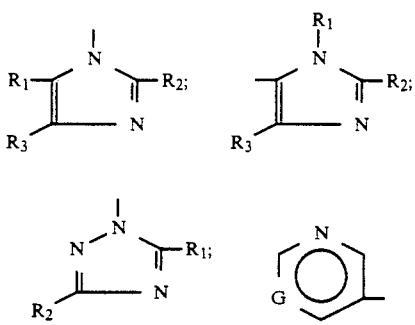

wherein:
- $R_1$, $R_2$, $R_3$, which may be either equal to, or different from, one another, are:
  H, $(C_1-C_6)$-alkyls, $(C_1-C_6)$-haloalkyls, $(C_2-C_6)$-alkenyls, $(C_2-C_6)$-haloalkenyls, $(C_2-C_6)$-alkinyls, $(C_2-C_6)$-haloalkinyls; and
- G represents either CH or N.

The following are further objects of the present invention:
- salts of the compounds of general formula (I) derived from an inorganic acid such as a halide acid, for example hydroiodic acid, hydrobromic acid, hydrochloric acid; sulfuric acid, nitric acid, thiocyanic acid and phosphoric acid; or from an organic acid, such as acetic acid, propionic acid, ethanedioic acid, propanedioic acid, benzoic acid, methanesulfonic acid, 4-methylbenzenesulfonic acid, and so forth; and
- metal complexes obtained by a complexation reaction between the derivatives of type (I) with an organic or inorganic metal salt, such as a halide, a nitrate, a sulfate, a phosphate of, e.g., copper, manganese, zinc or iron.

Examples of compounds of general formula (I), according to the present invention, are reported in the following Table 1:

TABLE 1

| | Ar | X, K, Z | $B_1$ | $B_2$ | Rhl | A |
|---|---|---|---|---|---|---|
| 1 | 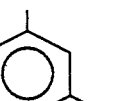 phenyl-CF₃ | 0, 0, 0 | —CH₂CH₂— | —CH₂CH₂— | —CF₂CF₂H | imidazole |
| 2 | 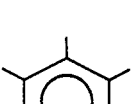 2,4,6-trichlorophenyl | 0, 0, 0 | —CH₂CH₂— | —CH₂CH₂— | —CF₂CF₂H | imidazole |
| 3 |  4-chlorophenyl | 0, 0, 0 | —CH₂CH₂— | —CH₂CH₂— | —CF₂CF₂H | imidazole |

TABLE 1-continued

| | Ar | X, K, Z | B₁ | B₂ | Rhl | A |
|---|---|---|---|---|---|---|
| 4 | 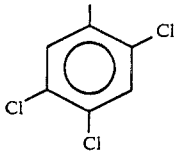 2,4,5-trichlorophenyl | 0, 0, 0 | —CH₂CH₂— | —CH₂CH₂— | —CF₂CF₂H | 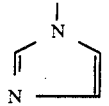 imidazole |
| 5 | 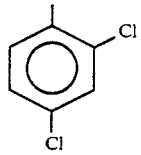 2,4-dichlorophenyl | 0, 0, 0 | —CH₂CH₂— | —CH₂CH₂— | —CF₂CF₂H | 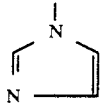 imidazole |
| 6 | 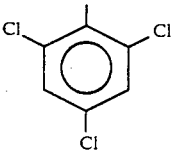 2,4,6-trichlorophenyl | 0, 0, 0 | —CH₂CH₂— | —CH₂CH₂— with CH₃ branch | —CF₂CF₂H | 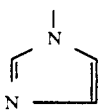 imidazole |
| 7 | 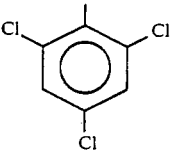 2,4,6-trichlorophenyl | 0, 0, 0 | —CH₂CH₂— | —CH₂CH₂CH₂— | —CF₂CF₂H | 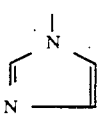 imidazole |
| 8 | 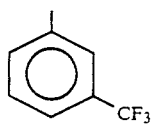 3-CF₃-phenyl | 0, 0, 0 | —CH₂CH₂— | —CH₂CH₂— | —CF₂CFHOCF₃ | 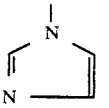 imidazole |
| 9 | 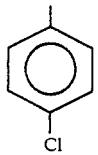 4-chlorophenyl | 0, 0, 0 | —CH₂CH₂— | —CH₂CH₂— | —CF₂CF₂H | 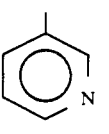 pyridine |
| 10 |  4-OCF₂CF₂H-phenyl | 0, 0, 0 | —CH₂CH₂— | —CH₂CH₂— | —CF₂CF₂H— | 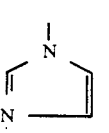 imidazole |
| 11 | 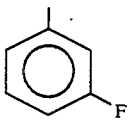 3-fluorophenyl | 0, 0, 0 | —CH₂CH₂— | —CH₂CH₂— | —CF₂CF₂H— | 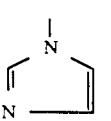 imidazole |
| 12 | 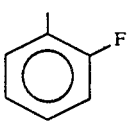 2-fluorophenyl | 0, 0, 0 | —CH₂CH₂— | —CH₂CH₂— | —CF₂CF₂H— | 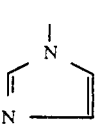 imidazole |

TABLE 1-continued

| | Ar | X, K, Z | B₁ | B₂ | Rhl | A |
|---|---|---|---|---|---|---|
| 13 | 4-tert-butylphenyl | 0, 0, 0 | —CH₂CH₂— | —CH₂CH₂— | —CF₂CF₂H— | imidazolyl |
| 14 | 2,4-dichlorophenyl | 0, 0, 0 | —CH₂CH₂— | —CH₂CH₂— | —CF₂CFClH | imidazolyl |
| 15 | 2,4,6-trichlorophenyl | 0, 0, 0 | —CH₂CH₂— | —CH₂CH₂— | —CF₂CF₂H— | 1-methylimidazolyl |

Compounds of the general formula (I) may be prepared by several synthesis routes, some of which are summarized in the following schemes:

SYNTHESIS ROUTE (1)

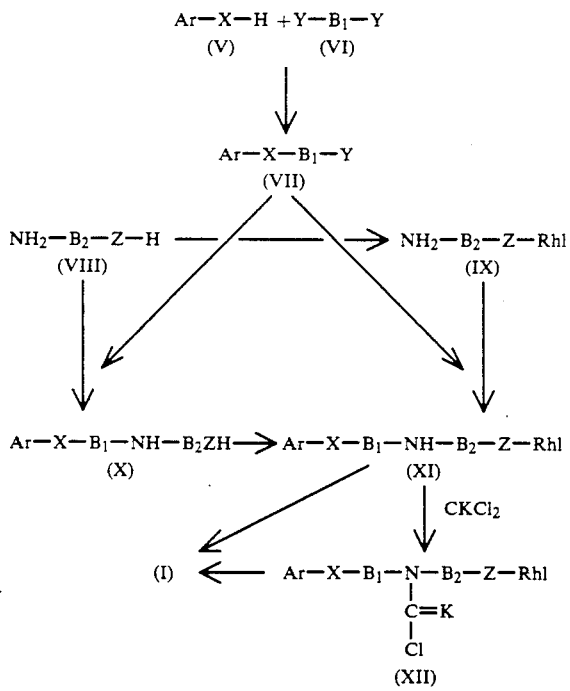

wherein:
Y = a leaving group, such as, e.g., a halogen or a sulfonic acid ester.

According to the above scheme (1), the compound (VII) is obtained by the reaction of the compound (V) with the compound (VI), in the presence of a base, such as, e.g., sodium hydroxide or potassium hydroxide, sodium hydride, potassium tert.-butoxide, or of an alkali-metal carbonate to which a phase-transfer catalyst is added, in suitable solvents, such as, e.g., water or such alcohols as methanol, ethanol, butanol, ethylene glycol, or, in case the reaction is to be carried out under phase-transfer conditions, in an aprotic polar solvent, such as, e.g., dimethylformamide, methyl-pyrrolidone, or in an aromatic solvent, such as toluene, or in a halogenated solvent such as, e.g., methylene chloride or dichloroethane.

The reaction temperatures may be within the range of from 0° C. up to the boiling temperature of the solvent, as described in Organic Synthesis, Coll. vol. I, page 435.

The compound (V) may also be used in salified form with alkali metals or alkaline-earth metals.

The compound (VII) is then reacted with an amine (VIII) or with an amine (IX), in the presence of either an inorganic or an organic base, such as, e.g., an alkali metal hydroxide, carbonate or bicarbonate, triethylamine or pyridine, or by using an excess of the amine (VIII) or (IX) as an acid acceptor, by operating in solvents, and under conditions which are analogous to those indicated in the previous step.

According to the amine used, the intermediate (X) or the intermediate (XI) are, respectively, obtained.

The intermediate (XI) is then reacted with a carbonyl derivative of the nitrogen-containing heterocyclic compound (A), e.g., with carbonyl-diimidazole in aromatic or halogenated solvents, at temperatures within the range of from 0° C. up to boiling temperature of the solvent, in order to obtain the compound (I).

According to a different route, the compound (XI) is reacted with phosgene or thiophosgene in such organic solvents as ethyl acetate, with the compound (XII) being thus obtained, from which, by means of subsequent reaction with a nitrogen-containing heterocyclic of the (A) type, for example imidazole, the compound (I) is obtained.

According to an alternative route, the compound (XI) is reacted with the chloride of a nicotinic acid in order to obtain the compound (I).

The intermediate compound (XI) may also be obtained:

by the reaction of addition of the compound (X) to a polyfluoroolefin, for example of the $CF_2=CX_1X_2$ type, wherein
$X_1 = Cl, F, CF_3, OCF_3$, and
$X_2 = F, CF_3$, in the presence of catalytic or stoichiometric amounts of strong bases, such as sodium hydride or potassium tert.-butoxide, in such dipolar aprotic solvents as dimethylsulfoxide, dimethylformamide, or in an alcoholic solvent, such as, e.g., tert.-butanol, at temperatures within the range of from $-20°$ C. up to $100°$ C.; or by the reaction of an alkaline-metal salt of the compound (X) with compound of the Y-Rhl type, wherein Y is a suitable leaving group such as a halogen or a sulfonic ester.

In a similar way, the amine (IX) may be obtained from the compound (VIII) by means of the same methods as reported above for compound (XI).

The compounds which contain an -Rhl group in which at least one hydrogen atom and more than one halogen atom are present, may be transformed into the corresponding unsaturated compounds by dehydrohalogenation.

SYNTHESIS ROUTE (2)

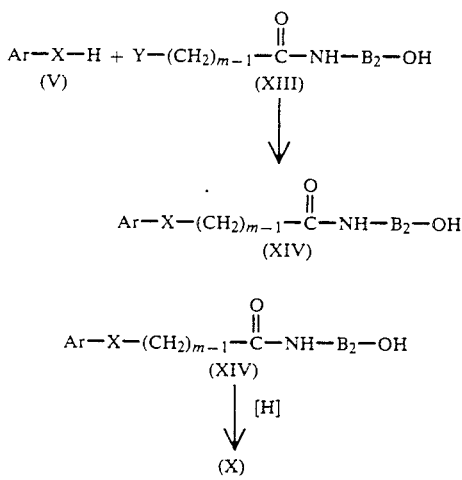

wherein: $m = 1-6$.

According to the above synthesis route (2), the amide (XIV) is obtained by reacting the compound (XIII) with the compound (V), in the presence of either organic or inorganic bases, in such solvents as methanol, ethanol, ethylene glycol, polyethyleneglycols, dimethylformamide, or under phase-transfer conditions.

The compound (XIV) is subsequently reduced to yield the compound (X), e.g., by using lithium-aluminum hydride in solvents of the ether type, such as tetrahydrofuran, and the intermediate (X) is then transformed into the compound (I) by following one of such routes as shown in the above Synthesis Route (1).

SYNTHESIS ROUTE (3)

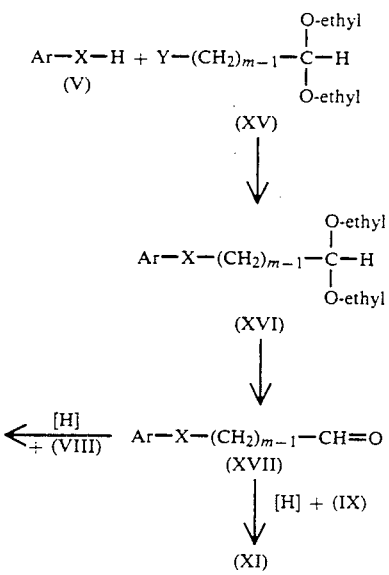

wherein: $m = 1-6$.

According to the Synthesis Route (3), by reacting compounds of type (XV) with compounds (V) the acetal (XVI) is obtained, from which by the subsequent unblocking the aldehyde (XVII) is obtained, which is reacted with the amine (VIII), in the presence of reducing systems, such as, e.g., hydrogen and catalysts, e.g., Pt or Pd, in organic solvents such as, e.g., methyl alcohol, under neutral conditions or under acidic conditions, e.g., by sulfuric acid, in order to yield the compound (X) from which, by following such routes as shown under the above Synthesis Route (1), the compound (I) is obtained.

As an alternative, the aldehyde (XVII) is used for the reducing alkylation of the amine (IX), e.g., with sodium cyano-boron-hydride under conditions known per se from the pertinent technical literature, in order to yield the compound (XI), which is then converted into the compound (I) by following one of the above described synthesis routes.

The compounds of general formula (I) are very powerful inhibitors of the growth of several species of pathogenic fungi which attack the cultivations of useful plants. They shown both a preventive activity and a curative activity when applied to useful plants or to parts thereof, such as, e.g., the leaves, and are particularly efficacious in preventing diseases caused by biotrophic pathogen fungi, such as, e.g., those belonging to the *Erysiphe* genus and to the *Puccinia* genus.

Examples of plant diseases which may be fought with the compounds according to the present invention are the following:

*Erysiphe graminis* on cereals;
*Sphaeroteca fulicinea* on cucurbits (e.g. cucumber);
*Puccinia* on cereals;
*Septoria* on cereals;
*Helminthosporium* on cereals;
*Rhynchosporium* on cereals;
*Podosphaera leucotricha* on apple tree;
*Uncinula necator* on vine;
*Venturia inaequalis* on apple tree;
*Piricularia oryzae* on rice;

Botrytis cinerea;
Fusarium on cereals;
as well as other plant diseases.

For practical uses in agriculture, it is often advantageous to have available fungicidal compositions containing one or more compounds of formula (I) as their active ingredient.

The application of these compositions may take place on any parts of the plants; for example, on leaves, stems, branches and roots, or on seeds before sowing, or also on the ground on or near where the plant grows.

Compositions may be used which are in the form of dry powders, wetting powders, emulsifiable concentrates, pastes, granulates, solutions, suspensions, and so forth; the selection of the type of compositions will depend on the specific use contemplated. These compositions are prepared in a per se known way, e.g., by diluting or dissolving the active substance with a solvent medium and/or a solid diluent optionally in the presence of surfactants. As solid diluents or supports, the following may be used: silica, kaolin, bentonite, talc, fossil flour, dolomite, calcium carbonate, magnesia, gypsum, clays, synthetic silicates, attapulgite, sepiolite. As liquid diluents, besides water various types of solvents may be used, for example aromatic solvents (benzene, xylenes or blends of alkylbenzenes), chloroaromatic solvents (e.g., chlorobenzene), paraffins (petroleum fractions), alcohols (e.g., methanol, propanol, butanol), amines, amides (e.g., dimethylformamide), ketones (e.g., cyclohexanone, acetophenone, isophorone, ethylamyl-ketone), esters (e.g., isobutyl acetate).

As surfactants: sodium, calcium or triethanolamine salts of alkylsulfates, alkylsulfonates, alkyl-aryl-sulfonates, polyethoxylated alkylphenols, fatty alcohols condensed with ethylene oxide, polyethoxylated fatty acids, polyethoxylated sorbitol esters, polyethoxylated fats, lignin-sulfonates may be used. The compositions may also contain special additives for particular purposes., e.g., such bonding agents as gum arabic, polyvinyl alcohol, polyvinylpyrrolidone.

If desired, to the compositions according to the present invention other compatible active substances such as fungicides, plant protection products, phytoregulators, herbicides, insecticides, fertilizers, may also be added.

The concentration of active substance in the said compositions may vary over a wide range, according to the active compound, the culture, the pathogenic agent, the environmental conditions, and the type of formulation to be adopted. In general, the concentration of active substance is within the range of from 0.1 to 95%, and preferably from 0.5 to 90%, by weight.

EXAMPLES

The following examples are supplied in order still better to illustrate the invention, but without implying any unnecesary limitations in the scope thereof:

EXAMPLE 1

Synthesis of
N-2-(1,1,2,2-tetrafluoro-ethoxy)-ethyl-N-[2-(3-trifluoromethyl-phenoxy)ethyl]-1-carboxyamido-imidazole (Compound 1)

To a solution of 1.3 grams of N-2-(1,1,2,2-tetrafluoroethoxy)-ethyl-N-[2-(3-trifluoromethyl-phenoxy)ethyl]-amine in 9 cc of toluene, 0.73 g of carbonyl-diimidazole is added. The mixture is kept stirred for 8 hours at 80° C., under a nitrogen blanketing atomosphere. After eliminating the reaction solvent by evaporation under reduced pressure, the residue is collected with methylene chloride. The solution is washed with water, dried over sodium sulfate, and evaporated under reduced pressure. The raw material thus obtained is purified by means of chromatography on silica, with a 95:5 (volume/volume=V/V) mixture of $CH_2Cl_2$: MeOH as the eluent.

1.2 g is obtained of an oil, the spectroscopic characteristics of which are consistent with Compound 1.

$^1$H-NMR (60 MHz) in $CDCl_3$:

| $\delta =$ 3.93 | (2H, t) |
|---|---|
| 3.96 | (2H, t) |
| 4.25 | (4H, t) |
| 6.13 | (1H, tt) |
| 7.00–7.50 | (6H, m) |
| 8.00 | (1H, s) |

EXAMPLE 2

Synthesis of
N-2-(1,1,2,2-tetrafluoro-ethoxy)-ethyl-N-2-(3-trifluoromethyl-phenoxy)ethyl]-amine To a solution of 2.0 grams of 2-[2-(3-trifluoromethyl-phenoxy)-ethylamine]-ethanol in 14 cc of dimethylsulfoxide, cooled at 5° C., 0.35 g of potassium tert.-butoxide is added. To the reaction flask tetrafluoroethylene is charged; the development of a slight exothermic heat is observed. The reaction mixture is kept standing for some hours under an atmosphere of the same gas (tetrafluoroethylene) the solution is then quenched by pouring into deionized water and the whole is extracted with methylene chloride. The organic phase is dried over sodium sulfate and is evaporated. 1.3 g of an oily residue is obtained.

$^1$H-NMR (60 MHz) in $CDCl_3$:

| $\delta =$ 2.83 | (2H, t) |
|---|---|
| 2.90 | (2H, t) |
| 4.03 | (4H, t) |
| 5.70 | (1H, tt) |
| 7.00–7.50 | (4H, m) |

EXAMPLE 3

Synthesis of
2-2-(3-trifluoromethyl-phenoxy)ethylamino]-ethanol 17.7 g of 1-bromo-2-(3-trifluoromethyl-phenoxy)ethane is added dropwise to a solution of 14.1 g of ethanolamine in 33 cc of ethanol. The mixture is kept stirred for 40 hours at room temperature, the solvent is then evaporated under reduced pressure and the residue is collected with 5 N NaOH (26 cc). The thus obtained solution is extracted with methylene chloride, which is subsequently washed with water, dried over sodium sulfate and evaporated to dryness. A white crystalline solid is obtained, which is collected with hexane, filtered and washed with the same solvent. 12.2 g of product is obtained.

$^1$H-NMR (60 MHz) in $CDCl_3$:

| $\delta =$ 2.95 | (2H, t) |
|---|---|
| 3.20 | (2H, t) |

| -continued | |
|---|---|
| 3.90 | (2H, t) |
| 4.35 | (2H, t) |
| 7.00–7.50 | (4H, m) |

EXAMPLE 4

Synthesis of
1-bromo-2-(3-trifluoromethylphenoxy)ethane

A solution of NaOH at 33% (17 cc) is added dropwise to a solution of 3-trifluoromethylphenol (2.5) and 1,2-dibromoethane (30.0 g) in deionized water (30 cc). The resulting mixture is kept under refluxing conditions for 7 hours. The reaction mixture is then cooled, the oil formed is separated from the aqueous phase and distilled under a pressure of 15 mm Hg. The fraction within the range of from 118° to ° C. is collected. 26 g of the desired product is obtained.
$^1$H-NMR (60 MHz) in CDCl$_3$:

| $\delta =$ 2.95 | (2H, t) |
|---|---|
| 3.20 | (2H, t) |
| 3.90 | (2H, t) |
| 4.35 | (2H, t) |
| 7.00–7.50 | (4H, m) |

EXAMPLE 5

Synthesis of
N-2-(1,1,2,2-tetrafluoroethoxy)-ethyl]-N-2-(2,4,6-trichlorophenoxy)-ethyl]-1-carboxyamido-imidazole (Compound 2)

The process is carried out in the same way as in Example 1, starting from N-[2-(1,1,2,2-tetrafluoroethoxy)-ethyl]-N-[2-(2,4,6-trichlorophenxoy)-ethyl)-amine
$^1$H-NMR (60 MHz) in CDCl$_3$:

| $\delta =$ 3.90 | (4H, m) |
|---|---|
| 4.20 | (4H, m) |
| 5.66 | (1H, tt) |
| 7.00–7.44 | (3H, s) |
| 7.90 | (1H, s) |

EXAMPLE 6

Synthesis of
N-[2-(1,1,2,2-tetrafluoroethoxy)-ethyl]-N-[2-(2,4,6-trichlorophenxoy)-ethyl]amine The process is carried out in the same way as in Example 2, starting from 2-[2-(2,4,6-trichlorophenoxy)-ethyl)amino]-ethanol
$^1$H-NMR (60 MHz) in CDCl$_3$:

| $\delta =$ 2.95 | (2H, t) |
|---|---|
| 3.05 | (2H, t) |
| 4.10 | (4H, t) |
| 5.66 | (1H, tt) |
| 7.33 | (2H, s) |

EXAMPLE 7

Synthesis of 2-2-(2,4,6-trichlorophenoxy)-ethylamino]-ethanol

The process is carried out in the same way as in Example 3, starting from 1-bromo-2-(2,4,6-trichlorophenoxy)-ethane
$^1$H-NMR (60 MHz) in CDCl$_3$:

| $\delta =$ 2.70 | (2H, t) |
|---|---|
| 2.87 | (2H, t) |
| 3.65 | (2H, t) |
| 4.40 | (2H, t) |
| 7.72 | (2H, s) |

EXAMPLE 8

Synthesis of 1-bromo-2-(2,4,6,trichlorophenxoy)-ethane

The process is carried out in the same way as in Example 4, starting from 2,4,6-trichlorophenol
$^1$H-NMR (60 MHz) in CDCl$_3$:

| $\delta =$ 3.65 | (2H, t) |
|---|---|
| 4.30 | (2H, t) |
| 7.31 | (2H, s) |

EXAMPLES 9–14

By operating according to a procedure analogous to that of Example 1, the following compounds were prepared by starting from the corresponding amines.

Compound 3

N-2-(1,1,2,2-tetrafluoroethoxy)-ethyl-N-[2-(4-chlorophenoxy)-ethyl]-1-carboxyamido-imidazole
$^1$H-NMR (60 MHz) in CDCl$_3$:

| $\delta =$ 3.90 | (4H, m) |
|---|---|
| 4.20 | (4H, m) |
| 5.60 | (1H, tt) |
| 6.60–7.40 | (4H, m) |
| 8.00 | (1H, s) |

Compound 4

N-2-(1,1,2,2-tetrafluoroethoxy)-ethyl-N-[2-(2,4,5-trichlorophenoxy)-ethyl]-1-carboxyamido-imidazole
$^1$H-NMR (60 MHz) in CDCl$_3$:

| $\delta =$ 3.95 | (4H, m) |
|---|---|
| 4.20 | (4H, m) |
| 5.70 | (1H, tt) |
| 6.95–7.50 | (4H, m) |
| 8.00 | (1H, s) |

Compound 5

N-2-(1,1,2,2-tetrafluoroethoxy)-ethyl-N-[2-(2,4-dichlorophenoxy)-ethyl]-1-carboxyamido-imidazole
$^1$H-NMR (60 MHz) in CDCl$_3$:

| $\delta =$ 4.05 | (4H, m) |
|---|---|
| 4.30 | (4H, m) |
| 5.70 | (1H, tt) |
| 6.90–7.50 | (5H, m) |
| 8.00 | (1H, s) |

Compound 6

N-2-(1,1,2,2-tetrafluoroethoxy)-propyl-N-[2-(2,4,6-trichlorphenoxy)-ethyl]-1-carboxyamido-imidazole $^1$H-NMR (60 MHz) in CDCl$_3$:

| δ = | 1.35 | (3H, d) |
|---|---|---|
| | 3.6–4.30 | (7H, m) |
| | 5.70 | (1H, tt) |
| | 7.50 | (4H, m) |
| | 8.00 | (1H, s) |

Compound 7

N-3-(1,1,2,2-tetrafluoroethoxy)-propyl-N-[2-(2,4,6-trichlorophenoxy)-ethyl]-1-carboxyamido-imidzole $^1$H-NMR (60 MHz) in CDCl$_3$:

| δ = | 2.15 | (2H, m) |
|---|---|---|
| | 3.80 | (4H, m) |
| | 4.10 | (4H, m) |
| | 5.65 | (1H, tt) |
| | 7.00–7.40 | (4H, m) |
| | 7.95 | (1H, s) |

Compound 8

N-2-(1,1,2-trifluoro-2-trifluoromethoxy-ethoxy)-ethyl-N-[2-(3-trifluoromethylphenoxy)-ethyl]-1-carboxyamido-imidazole $^1$H-NMR (60 MHz) in CDCl$_3$:

| δ = | 3.90 | (4H, m) |
|---|---|---|
| | 4.60 | (4H, m) |
| | 5.65 | (1H, dt) |
| | 6.90–7.60 | (6H, m) |
| | 8.00 | (1H, s) |

EXAMPLE 15

Synthesis of
N-2-(1,1,2,2-tetrafluoroethoxy)-ethyl-N-[2-(4-chlorophenoxy)ethyl)-3-carboxyamido-pyridine (Compound 9)

To a solution of N-2-(1,1,2,2-tetrafluoroethoxy)-ethyl-N-[2-(4-chlorophenoxy)-ethyl]-amine (1.0 g) and of nicotinoyl chloride (0.56 g) in methylene chloride (6.5 cc), triethylamine (6.9 g) is slowly added dropwise.

The reaction mixture is kept overnight with stirring at room temperature. The reaction mixture is then treated with water, the organic phase is separted, dried and evaporated under reduced pressure.

The so-obtained mixture is purified by chromatograph on silica, using as the eluent a 95:5 (V:V) mixture of CH$_2$Cl$_2$:MeOH. 0.5 g is obtained of an oil, the spectroscopic characteristics of which are consistent with Compound 9.

$^1$H-NMR (60 MHz) in CDCl$_3$:

| δ = | 3.90 | (4H, m) |
|---|---|---|
| | 4.20 | (4H, m) |
| | 5.75 | (1H, tt) |
| | 6.60–8.00 | (7H, m) |
| | 8.65 | (1H, s) |

(Compound 10)

N-(1,1,2,2-tetrafluoroethoxy)ethyl)-N-(2-(4-(1,1,2,2-tetrafluoroethoxyphenoxy)ethyl)-1-carboxyamido-imidazole $^1$H-NMR (60 MHz) in CDCl$_3$:

| δ = | 3.90 | (4H, m) |
|---|---|---|
| | 4.20 | (4H, m) |
| | 5.65 | (1H, tt) |
| | 5.87 | (1H, tt) |
| | 6.7–7.3 | (5H, m) |
| | 7.97 | (1H, s) |

(Compound 11)

N-(2-(1,1,2,2-tetrafluoroethoxy)ethyl)-N-(2-(3-fluorophenoxy)ethyl)-1-carboxyamido-imidazole $^1$H-NMR (60 MHz) in CDCl$_3$:

| δ = | 3.80 | (4H, m) |
|---|---|---|
| | 4.25 | (4H, m) |
| | 5.75 | (1H, tt) |
| | 6.50–7.55 | (5H, m) |
| | 8.05 | (1H, s) |

(Compound 12)

N-(2-(1,1,2,2-tetrafluoroethoxy)ethyl)-N-(2-(2-fluorophenoxy)ethyl)-1-carboxyamido-imidazole $^1$H-NMR (60 MHz) in CDCl$_3$:

| δ = | 3.85 | (4H, m) |
|---|---|---|
| | 4.15 | (4H, m) |
| | 5.60 | (1H, tt) |
| | 6.80–7.40 | (5H, m) |
| | 7.93 | (1H, s) |

(Compound 13)

N-(2-(1,1,2,2-tetrafluoroethoxy)ethyl)-N-(2-(4-terbutylphenoxy)ethyl1-1-carboxyamido-imidazole $^1$H-NMR (60 MHz) in CDCl$_3$:

| δ = | 1.4 | (9H, ls) |
|---|---|---|
| | 3.87 | (4H, m) |
| | 4.20 | (4H, m) |
| | 5.60 | (1H, tt) |
| | 6.75–7.45 | (5H, m) |
| | 8.00 | (1H, s) |

(Compound 14)

N-(2-(1,1,2-trifluoro-2-chloroethoxy)ethyl)-N-(2-(2,4,6-trichlorophenyl)ethyl)-1-carboxyamido-imidazole $^1$H-NMR (60 MHz) in CDCl$_3$:

| δ = | 4.00 | (8H, m) |
|---|---|---|
| | 6.00 | (1H, dt) |
| | 6.60–7.30 | (6H, m) |
| | 7.90 | (1H, s) |

EXAMPLE 16

Synthesis of
N-(2-(1,1,2,2-tetrafluoroethoxy)ethyl)-N-(2-(2,4,6-trichlorophenoxy)ethyl)-5-carboxyamido-1-methylimidazole (Compound 15)

A solution of 1-methyl-5-carboxy-imidazole (1.0 g) and of thionyl chloride (30 cc) is kept under refluxing conditions for 2 hours, the excess of thionyl chloride is then evaporated under reduced pressure and the residue is collected with pyridine (15 cc); to the obtained solution cooled at 0° C., is slowly added dropwise a solution of N-(2-(1,1,2,2-tetrafluoroethoxy)ethyl)-N-(2-(2,4,6 trichlorophenoxy)ethyl) amine (2.5 g) in pyridine (5 cc). The mixture is kept stirred for 18 hours at room temperature and then it is collected with water and extracted with methylene chloride.

The organic phase is dried over sodium sulphate and evaporate-d under reduced pressure. The raw material thus obtained is purified by means of chromatography on silica, with a 97:3 (volume/volume=v/v) mixture of $CH_2Cl_2$: MeOH as the eluent.

0.85 g is obtained of a solid product, the spectroscopic characteristics of which are consistent with compound 15.

$^1$H-NMR (60 MHz) in $CDCl_3$:

| $\delta =$ 3.70 | (3H, s) |
|---|---|
| 4.10 | (8H, m) |
| 5.73 | (1H, tt) |
| 7.31 | (2H, s) |
| 7.36 | (1H, s) |

EXAMPLE 17

Determination of fungicial activity on oidium of wheat (*Erysiphe Graminis D.C.*)

Preventive Activity

Leaves of wheat cv. Irnerio, grown in pot inside a conditioned room, were treated by sprinkling both leaf faces with products to be tested in water-acetone solution at 20% (V/V) of acetone.

After 1 day in a conditioned room at 20° C. and 70% R.H., an aqueous suspension of *Erysiphe graminis* (200,000 conidia/cc) was sprinkled on both leaf faces of the leaves of the plants.

After 24 hours in a saturated-humidity atomosphere, at 21° C., the plants were left standing inside a conditioned room for the incubation of the fungus.

At the end of the incubation time (12 days), the extent of the infection was assessed visually, according to a scale ranging from 100 (sound plant) to 0 (completly infected plant).

Curative Activity

Leaves of wheat cv. Irnerio, grown in pot inside a conditioned room, were treated by sprinkling an aqueous suspension of *Erysiphe graminis* (200,000 conidia/cc) on both leaf faces of all of their leaves.

After 24 hours in a saturated-humidity atmosphere at 21° C., the leaves of the plants were treated by sprinkling the products to be tested in water-acetone solution at 20% (V/V) of acetone on both leaf faces of all of their leaves.

At the end of the incubation time (12 days), the extent of the infection was assessed visually, according to a scale ranging from 100 (sound plant) to 0 (completely infected plant).

The results are reported below in Table 2.

EXAMPLE 18

Determination of fungicidal activity on linear rust of wheat (*Puccinia graminis* Pers.)

Preventative Activity

Leaves of wheat cv. Irnerio, grown in pot inside a conditioned room, were treated by sprinkling the tested products in water-acetone solution at 20% (V/V) of acetone on both leaf faces of all of their leaves.

After 1 day in a conditioned room at 23° C. and 70%R.H., a mixture of spores of *Puccinia graminis* in talc (100 mg of spores per 5 g of talc) was sprinkled on both leaf faces of all plant leaves.

After 48 hours in a saturated-humidity atmosphere, at 21° C., the plants were stored in a conditioned room for fungus incubation.

At the end of the incubation time (14 days), the extent of the infection was assessed visually, according to a scale ranging from 100 (sound plant) to 0 (completely infected plant).

Curative Activity

Leaves of wheat cv. Irnerio, grown in pot inside a conditioned room, were treated by sprinkling a mixture of spores of *Puccinia graminis* in talc (100 mg of spores per 5 g of talc) on both leaf faces of all of their leaves. After 48 hours in a saturated-humidity atmosphere, at 21° C., the leaves were treated by sprinkling a water T-M acetone solution at 20% of acetone (V/V) of the products to be tested on both leaf faces.

At the end of the incubation time (14 days), the extent of the infection was assessed visually according to a scale ranging from 100 (sound plant) to 0 (completely infected plant).

The results are reported below in Table 2.

TABLE 2

| Compound N. | Dose, g/l | *Erysiphe graminis* Wheat | | *Puccinia graminis* Wheat | |
|---|---|---|---|---|---|
| | | Preventive activity | Curative activity | Preventive activity | Curative activity |
| 1 | 1.0 | 97 | 100 | 80 | 100 |
| | 0.5 | 90 | 100 | 70 | 100 |
| | 0.125 | 85 | 95 | 40 | 90 |
| 2 | 1.0 | 100 | 100 | 60 | 95 |
| | 0.5 | 97 | 100 | 40 | 80 |
| | 0.125 | 90 | 100 | 20 | 40 |
| Ref.* | 1.0 | 97 | 100 | 40 | 60 |
| | 0.5 | 85 | 95 | 10 | 40 |
| | 0.125 | 60 | 85 | 0 | 10 |

*Ref. corresponds to the reference compound, N-propyl-N-[2-(2,4,6-trichlorophenoxy)-ethyl]-1-carboxyamide-imidazole, known as Prochloraz (Sportak), U.S. Pat. No. 3,991,071.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A compound having the formula:

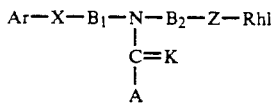

wherein:
- Ar represents a phenyl; a phenyl substituted with one or more halogens, $(C_1-C_3)$-alkyls, $(C_1-C_3)$-haloalkyls, $(C_2-C_4)$-alkenyls, $(C_2-C_4)$-haloalkenyls, $(C_1-C_3)$-alkoxy groups, $(C_1-C_4)$-haloalkoxy groups; a pyridyl, a pyridyl substituted with one or more halogens or with $(C_1-C_3)$-haloalkyls;
- K, X, Z, are, independently of each other, either O or S;
- $B_1$, $B_2$ which may be equal to or different from each other, are linear or branched $(C_1-C_6)$-alkylidenes;
- Rhl represents a $(C_1-C_6)$-haloalkyl containing from 1 to 9 halogen atoms, a $(C_2-C_8)$-haloalkenyl containing from 1 to 9 halogen atoms, $(C_3-C_8)$-haloalkoxyalkyls, $(C_3-C_8)$-haloalkoxyalkenyls;
- A represents

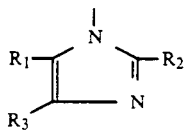

wherein:
- $R_1$, $R_2$, $R_3$ which may be either equal to, or different from one another, are: H, $(C_1-C_6)$-alkyls, $(C_1-C_6)$-haloalkyls, $(C_2-C_6)$-alkenyls, $(C_2-C_6)$-haloalkenyls, $(C_2-C_6)$-alkinyls, $(C_2-C_6)$-haloalkinyls.

2. A compound according to claim 1, wherein the halogens of Rhl are fluorine.

3. A compound according to claim 1, which is: N-2-(1,1,2,2-tetrafluoro-ethoxy)-ethyl-N-[2-(3-trifluoromethyl-phenoxy)ethyl]-1-carboxyamido-imidazole.

4. A compound according to claim 1, which is: N-[2-(1,1,2,2-tetrafluoroethoxy)-ethyl]-N-[2-(2,4,6-trichloro-phenoxy)-ethyl]-1-carboxyamido-imidazole.

5. A compound according to claim 1, which is: N-2-(1,1,2,2-tetrafluoroethoxy)-ethyl-N-[2-(4-chloro-phenoxy)ethyl]-1-carboxyamido-imidazole.

6. A compound according to claim 1, which is: N-2-(1,1,2,2-tetrafluoroethoxy)-ethyl-N-[2-(2,4,5-trichloro-phenoxy)-ethyl]-1-carboxyamido-imidazole.

7. A compound according to claim 1, which is: N-2-(1,1,2,2-tetrafluoroethoxy)-ethyl-N-[2-(2,4-dichloro-phenoxy)-ethyl]-1-carboxyamido-imidazole.

8. A compound according to claim 1, which is: N-2-(1,1,2,2-tetrafluoroethoxy)-propyl-N-[2-(2,4,6-trichlorophenoxy)-ethyl]-1-carboxyamido-imidazole.

9. A compound according to claim 1, which is: N-3-(1,1,2,2-tetrafluoroethoxy)-propyl-N-[2-(2,4,6-trichlorophenoxy)-ethyl]-1-carboxyamido-imidazole.

10. A compound according to claim 1, which is: N-2-(1,1,2-trifluoro-2-trifluoromethoxy-ethoxy)-ethyl-N-[2-(3-trifluoromethylphenoxy)-ethyl]-1-carboxyamido-imidazole.

11. Method for combating fungal infections in useful plants, consisting in distributing on the plant, on the seeds or on the surrounding soil, when the fungal infection is expected or is already in course, an effective amount of a compound according to any one of the claims from 1 to 10, as such or as a suitable composition.

12. An antifungal composition containing as an effective amount active ingredient at least one compound according to any one of the claims from 1 to 10, together with a solid or liquid carrier, and, optionally, other additives.

* * * * *